(12) United States Patent
Mizutani

(10) Patent No.: US 6,394,989 B2
(45) Date of Patent: *May 28, 2002

(54) ABSORBENT ARTICLE HAVING DEFORMATION INDUCING MEANS

(75) Inventor: Satoshi Mizutani, Kagawa-ken (JP)

(73) Assignee: Uni-Charm Corporation (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/161,022

(22) Filed: Sep. 25, 1998

(30) Foreign Application Priority Data

Sep. 29, 1997 (JP) .............................. 9-264654
Sep. 29, 1997 (JP) .............................. 9-264655

(51) Int. Cl.[7] .............................................. A61F 13/15
(52) U.S. Cl. ........................ 604/385.01; 604/385.201; 604/385.27; 604/385.26; 604/383
(58) Field of Search ................................ 604/347, 354, 604/385.1, 386, 385.2, 387, 378, 109, 49.4, 385.01, 385.201, 385.27, 385.26, 383

(56) References Cited

U.S. PATENT DOCUMENTS

| | | | | |
|---|---|---|---|---|
| 4,673,403 A | * | 6/1987 | Lassen et al. | 604/385 |
| 4,804,380 A | * | 2/1989 | Lassen et al. | 604/385.1 |
| 4,822,350 A | * | 4/1989 | Ito et al. | 604/372 |
| 4,846,824 A | * | 7/1989 | Lassen et al. | 604/385.1 |
| 4,897,084 A | * | 1/1990 | Ternstrom et al. | 604/385.2 |
| 4,911,701 A | * | 3/1990 | Mavinkurve | 604/385.2 |
| 5,080,658 A | * | 1/1992 | Igaue et al. | 604/385.2 |
| 5,129,893 A | * | 7/1992 | Thoren | 604/385.2 |
| 5,197,959 A | * | 3/1993 | Buell | 604/385.1 |
| 5,295,987 A | * | 3/1994 | Widlund et al. | 604/385.2 |
| 5,354,400 A | * | 10/1994 | Lavash et al. | 156/227 |
| 5,545,156 A | * | 8/1996 | DiPalma et al. | 604/385.1 |
| 5,558,656 A | * | 9/1996 | Bergman | 604/385.1 |
| 5,569,231 A | * | 10/1996 | Emenaker et al. | 604/385.1 |
| 5,591,150 A | * | 1/1997 | Olsen et al. | 604/385.1 |
| 5,624,421 A | * | 4/1997 | Dabi et al. | 604/378 |
| 5,688,259 A | * | 11/1997 | Osborn, III et al. | 604/385.1 |
| 5,722,967 A | * | 3/1998 | Coles | 604/385.1 |
| 5,827,258 A | * | 10/1998 | McFall et al. | 604/385.1 |
| 5,849,003 A | * | 12/1998 | Olsen et al. | 604/387 |
| 5,957,909 A | * | 9/1999 | Hammons et al. | 604/387 |
| 6,210,385 B1 | * | 4/2001 | Mizutani | 604/385.01 |

FOREIGN PATENT DOCUMENTS

| | | | | |
|---|---|---|---|---|
| EP | 0 214 636 | * | 3/1987 | 604/385.1 |
| EP | 0 360 285 | | 3/1990 | |
| EP | 0 572 033 | | 12/1993 | |
| GB | 2 296 437 | | 7/1996 | |
| JP | A-2-7958 | | 1/1990 | |
| JP | A-2-11138 | | 1/1990 | |
| JP | U-5-62228 | | 8/1993 | |
| JP | B2-6-40888 | | 6/1994 | |
| JP | A-9-507033 | | 7/1997 | |
| WO | 93/01783 | * | 2/1993 | 604/385.1 |
| WO | 95/00095 | * | 1/1995 | 604/385.1 |
| WO | WO 95/07674 | | 3/1995 | |
| WO | WO 95/17148 | | 6/1995 | |
| WO | WO 97/07764 | | 3/1997 | |

* cited by examiner

Primary Examiner—John G. Weiss
Assistant Examiner—Michael Bogart
(74) Attorney, Agent, or Firm—Baker & Daniels

(57) ABSTRACT

An absorbent article such as sanitary napkin having an absorbent laminate is provided on a skin-noncontactable side of the laminate with deformation inducing means. The deformation inducing means include a hydrophobic panel member and an elastically stretchable member adapted to pull the panel member toward its middle under contractile force of the elastically stretchable member and thereby to convexly deform the panel member toward a skin-contactable side of the laminate. Convex deformation of the panel member by the deformation inducing means allows the laminate to be convexly deformed.

14 Claims, 6 Drawing Sheets

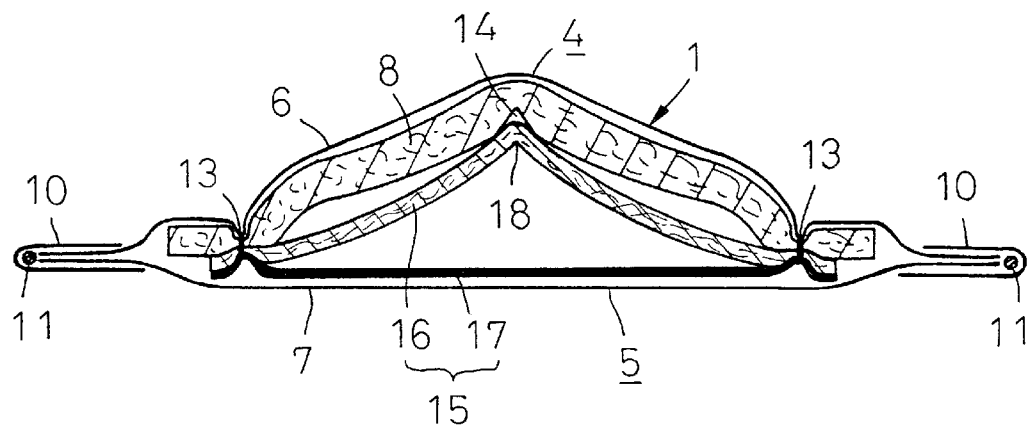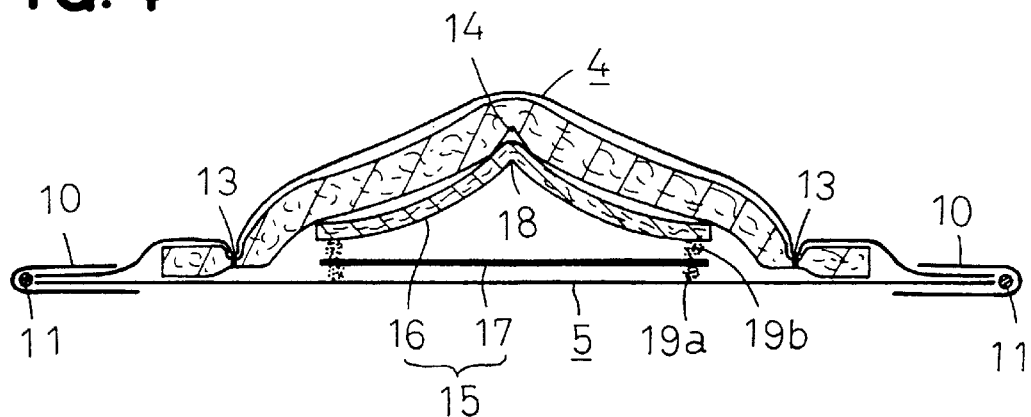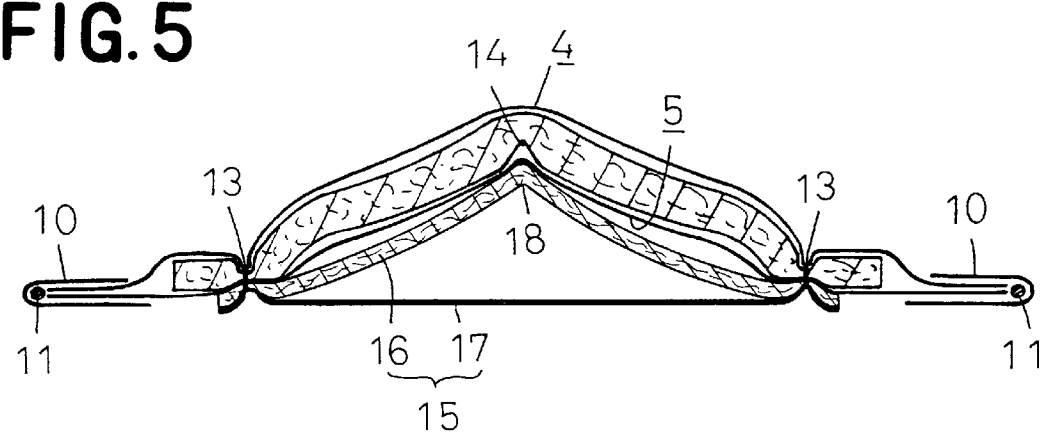

ABSORBENT ARTICLE HAVING DEFORMATION INDUCING MEANS

BACKGROUND OF THE INVENTION

This invention relates to disposable absorbent articles and particularly to sanitary napkins adapted for absorption and containing of menstrual discharge and incontinence pads for women.

Conventional sanitary napkins generally include an absorbent laminate consisting of a liquid-permeable topsheet, a liquid-impermeable backsheet and a liquid-absorbent core disposed between these two sheets. Sanitary napkins disclosed, for example, in Japanese Patent Publication (Kokoku) No. Hei6-40888, Japanese Patent Application Disclosure (Kokai) No. Hei2-7958 and Japanese Patent Application (PCT) Disclosure (Kohyo) No. Hei9-507033 includes an elastically stretchable member provided on the liquid-absorbent core so as to extend at least transversely thereof and to deform the napkin convexly toward the wearer's skin as the elastically stretchable member contracts. A sanitary napkin disclosed in Japanese Patent Application Disclosure (Kokai) No. Hei2-11138 includes a flexurally rigid element serving as a deforming element provided on a lower surface of the liquid-absorbent core so that the napkin may be normally forced by the element to be convexly deformed toward the wearer's skin. A sanitary napkin disclosed in Japanese Utility Model Application Disclosure No. Hei5-62228 includes an elastic member provided in a liquid-absorbent core adjacent its upper layer along a longitudinal center line so that the napkin may be convexly deformed toward the wearer's skin as the elastic member contracts longitudinally of the liquid-absorbent core.

In the case of the sanitary napkin disclosed by the above-mentioned Japanese Patent Publication No. Hei6-40888, Japanese Patent Application Disclosure No. Hei2-7958 and Japanese Patent Application (PCT) Disclosure No. Hei9-507033, the convex deformation occurs only under a contractile effect of the elastically stretchable member. So far as the liquid-absorbent core is not "collapsed" due to menstrual discharge absorbed therein or not deformed by an external force exerted thereon during use of the napkin, the convex deformation is maintained by the contractile effect of the elastically stretchable member. However, when the phenomenon of collapse as well as the deformation due to the external force is inevitable, the napkin is impossible to maintain the desired convex deformation since the convexity is lost or changed into another shape due to these factors.

According to the above-mentioned Japanese Patent Application Disclosure No. Hei2-11138, the convex deformation is obtained by a convex shape previously given to said deforming element. Such a sanitary napkin is necessarily bulky and this bulkiness may be alleviated by packaging the napkin so as to be compressed in a thickness direction of the napkin as in the conventional manner of packaging. However, if a period before unpacking is relatively long, the deforming element may not restore its original state sufficiently to deform the napkin with a desired convexity. While this inconvenience can be probably overcome by appropriately selecting the material for the deforming element, this selection will be considerably difficult. Furthermore, a predetermined flexural resistance is required to maintain the desired convex deformation and the material selected to meet this requirement has often a relatively high rigidity. In consequence, the napkin is provided with a correspondingly high rigidity which may give the wearer uncomfortable stiff feeling.

According to the above-mentioned Japanese Utility Model Application Disclosure No. Hei5-62228, the upper layer of the liquid-absorbent core tends to be lifted off the remainder underlying the upper layer under a contractile force of the elastic member. In consequence, body fluids discharged on the upper layer can not be adequately absorbed by the remainder layer and often stay on the upper layer until the body fluids leak laterally of the napkin.

SUMMARY OF THE INVENTION

In view of the above problems, it is an object of the invention to provide a sanitary napkin so improved to make effective use of the advantages offered by the known sanitary napkins and at the same time to eliminate the problems left unsolved by these sanitary napkins.

According to the invention, there is provided an absorbent article having a longitudinal center line, a transverse center line being orthogonal to the longitudinal center line, a skin-contactable side and a skin-noncontactable side, the absorbent article comprising: an absorbent laminate and deformation inducing means provided closely adjacent the skin-noncontactable side so as to convexly deform the absorbent laminate toward the skin-contactable side; the deformation inducing means including a hydrophobic panel member and an elastically stretchable member secured to the panel member parallel to the transverse center line or along the longitudinal center line so as to convexly deform the panel member toward the skin-contactable side as the elastically stretchable member elastically contracts; and respective regions of the absorbent laminate and the deformation inducing means having been convexly deformed being deformable to substantially flat states against a contractile force of the elastically stretchable member when a contacting pressure directed from the skin-contactable side toward the skin-noncontactable side is exerted on the article.

According to the invention, cooperation of the panel member and the elastically stretchable member constituting together the deformation inducing means causes the absorbent laminate to be convexly deformed toward the skin-contactable side and to be closely placed against the wearer's external genital organs. With a contacting pressure directed from the skin-contactable side to the skin-noncontactable side being exerted thereon, the absorbent laminate can be deformed together with the deformation inducing means to its flat state against the contractile force of the deformation inducing means.

BRIEF DESCRIPTION OF THE DRAWINGS

FIG. 3 is a schematic sectional view of the napkin taken along a line diving said napkin in front and rear halves;

FIG. 4 is a view schematic sectional similar to FIG. 3 but of a sanitary napkin according to a second embodiment of the invention;

FIG. 5 is a schematic sectional view to FIG. 3 but of a sanitary napkin according to a third embodiment of the invention;

DESCRIPTION OF THE PREFERRED EMBODIMENTS

Details of an absorbent article according to the invention will be more fully understood from the description of a sanitary napkin, one of specific embodiments of the invention given hereunder with reference to the accompanying drawings.

Figure 1:
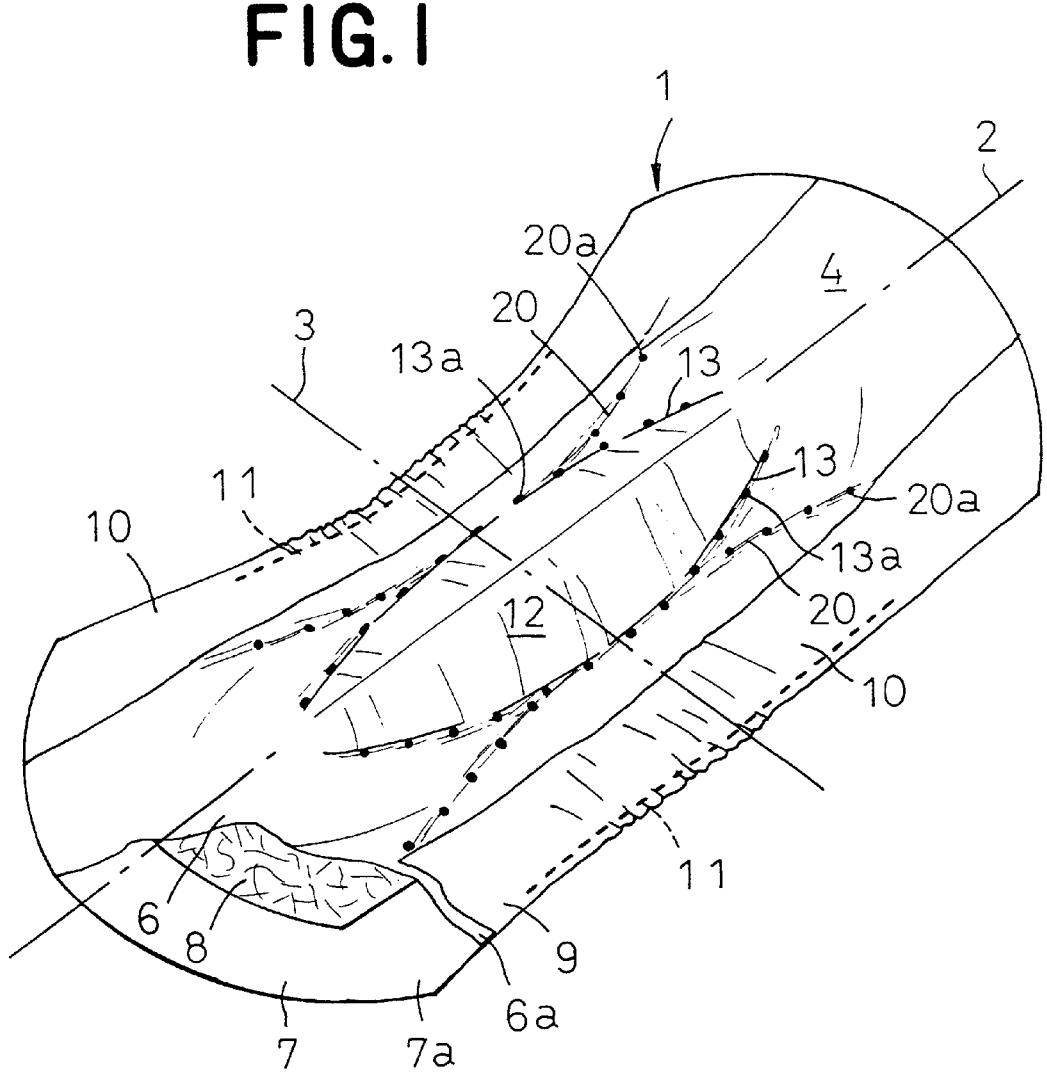
FIG. 1 is a perspective view of a sanitary napkin according to a first embodiment of the invention.
Figure 2:
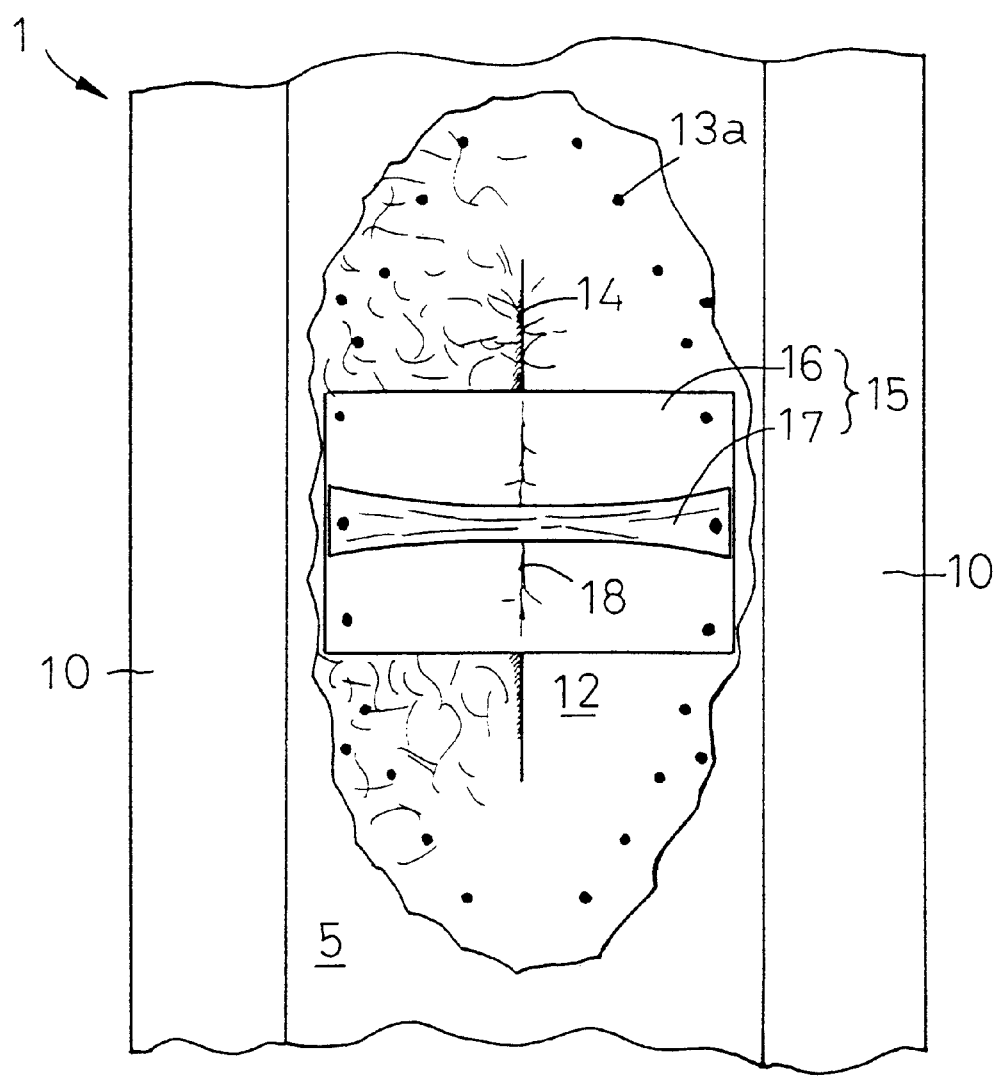
FIG. 2 is a plan view of a bottom side of the partly cutaway napkin.

FIGS. 1–3 illustrates a first embodiment of the invention. Referring to FIGS. 1–3, a sanitary napkin is provided in the form of an absorbent laminate 1 having a longitudinal center line 2, a transverse center line 3 being orthogonal to the longitudinal center line 2, a skin-contactable side 4 and a skin-noncontactable side 5. The absorbent laminate 1 is composed of a liquid-permeable topsheet 6, a liquid-impermeable backsheet 7 and a liquid-absorbent core 8 disposed between these two sheets 6, 7. Being larger than the core 8 in their longitudinal and transverse dimensions, both the topsheet 6 and the backsheet 7 extend outward beyond peripheral edges of the core 8. Transverse extensions 6a, 7a of the topsheet 6 and the backsheet 7 are covered with respective elongate sheets 9, 9 each folded in longitudinal halves so that each of the transverse extensions 6a, 7a is sandwiched between the longitudinal halves. In this manner, the transverse extensions 6a, 7a and the elongate sheets 9, 9 form together a pair of side flaps 10, 10. Each of these side flaps 10, 10 contains therein an elastically stretchable member 11 attached thereto along its outer edge so that the member 11 may be longitudinally contractile and thereby this side flap 10 may rise upward (toward the wearer's skin).

The topsheet 6, the backsheet 7 and the core 8 may be made of materials which have conventionally used for making well-known sanitary napkins and disposable diapers. The topsheet 6 may be made, for example, of a hydrophilic or hydrophobic nonwoven fabric, a porous plastic film or a laminate of these nonwoven fabric and plastic film. The backsheet 7 may be made, for example, of a moisture permeable plastic film or a laminate of this and a hydrophobic nonwoven fabric. The core 8 may be made, for example, of a mixture of fluff pulp and superabsorbent polymer powder. Employing these materials, both the topsheet 6 and the backsheet 7 have a high flexibility, on one hand, and the core 8 has a semi-rigidity, on the other hand. Though not shown, the topsheet 6 preferably has a plurality of liquid-guiding openings over its entire area. Of these liquid-guiding openings, those formed in a convexly deformable zone 12 which will be described later preferably have their diameters larger than those formed in the remaining zone so as to offer a correspondingly higher liquid-guiding ability. In addition, the topsheet 6 preferably contains an amount of thermoplastic fibers at least required to obtain a heat-sealing effect so far as the topsheet is made of a nonwoven fabric. The core 8 also may contain a thermoplastic fibers, if desired, unless its absorptivity is adversely thereby to an undesirable degree. The elongate sheet 9 may be made, for example, of a hydrophobic nonwoven fabric or a plastic film. The elastically stretchable member 11 may be made, for example, of natural rubber, synthetic rubber, spandex or the like.

The absorbent laminate 1 has a pair of deformation assisting means 13 longitudinally extending across a longitudinally as well as transversely middle region of this laminate 1, along a pair of lines that are curved outward symmetrically on both sides of the longitudinal center line 2. This pair of deformation assisting means 13 define a convexly deformable zone 12. The laminate 1 additionally has another pair of deformation assisting means 20 extending adjacent outer sides of the first-mentioned pair of deformation assisting means 13, respectively, describing lines curved inward symmetrically on both sides of the longitudinal center line 2. These pairs of deformation assisting means 13, 20 may be formed by respective series of compressed dots (i.e., embosses) or respective compressed grooves. The laminate 1 is further provided in the convexly deformable zone 12 with single deformation assisting means 14 extending on a bottom surface (i.e., on the skin-noncontactable side 5) of the core 8 along the longitudinal center line 2. While this deformation assisting means 14 is shown to be formed by a compressed groove, it is also possible to form this deformation assisting means 14 by a slit dividing the core 8 in two or a series of compressed dots (i.e., embosses). In the middle of the convexly deformable zone 12, the laminate 1 is provided on the bottom surface (i.e., on the skin-noncontactable side 5) with deformation inducing means 15. The deformation inducing means 15 include a rectangular hydrophobic panel member 16 and an elastically stretchable member 17 both extending transversely of the laminate 1. The panel member 16 is deformable to a substantially flat state and includes a middle portion 18 having a tendency to be folded (so-called potential fold) toward the skin-contactable side 4 along the longitudinal center line 2. The middle portion 18 of the panel member 16 extends in conformity with the compressed groove 14 functioning as the deformation assisting means for the core 8. The elastically stretchable member 17 is secured to the panel member 16 in the proximity of transversely opposite side edges of the panel member 16 under longitudinal tension. Consequently, the panel member 16 is convexly deformed toward the skin-contactable side 4 along the potential fold of the middle portion 18 as the elastically stretchable member 17 contracts. A lifting effect owing to this deformation of the panel member 16 causes the core 8 to be convexly deformed upward (i.e., toward the wearer's skin) together with the topsheet 6 in the convexly deformable zone 12 along the compressed groove 14 functioning as the deformation assisting means for the core 8. This deformation causes, in the convexly deformable zone 12, the core 8 to be spaced from the backsheet 7 and thereby a space is formed between these two components 7, 8. When a contacting pressure directed from the skin-contactable side 4 toward the skin-noncontactable side 5 is exerted on the laminate 1, the topsheet 6, the core 8 and the panel member 16 are deformed to a flat state against the contracting effect of the elastically stretchable member 17. With a consequence, the skin-contactable side 4 in the convexly deformable zone 12 tightly fits to the wearer's external genital organs and a leakage of menstrual discharge is effectively avoided. It should be understood that the contacting pressure and release thereof are more or less repeated as the wearer of the napkin moves her body. As a result, the space between the core 8 and the backsheet 7 is repeatedly collapsed and restored. This causes a pumping effect serving to expel an amount of water vapor or moisture staying in this space and in the vicinity thereof out from the napkin, on one hand, and to suck fresh atmospheric air into the napkin, on the other hand. In this way, an uncomfortable feeling due to water vapor or moisture is more or less alleviated.

The panel member 16 has its transversely opposite side edges extending outward slightly beyond the transversely opposite side edges of the deformation assisting means 13 and secured to the core 8 in the proximity of the transversely opposite side edges of the core 8 by means of the series of compressed dots (i.e., the heat-sealed dots formed by embossing) 13. Such securing may be achieved also by hot melt adhesive means instead of the heat-sealing.

The panel member 16 may be made, for example, of a paper sheet, a fibrous sheet, a foamed plastic sheet or a laminate consisting of at least two of these sheets. Depending on a particular bending resistance (i.e., rigidity) of the laminate 1, the panel member 16 generally has a cantilever measured value of 40~100 mm and preferably of 50~80 mm under the prescription according to the Japanese Industry Standard (JIS). The panel member 16 is of hydrophobic nature and can induce a desired deformation of the core 8 without suffering from so-called collapse phenomenon even when the panel member 16 is wetted with body fluids such as menstrual discharge. The elastically stretchable member 17 may be, for example, of natural rubber, synthetic rubber, spandex, an elastic foamed sheet or an elastic nonwoven fibrous sheet. Depending on a particular bending resistance (i.e., rigidity) of the absorbent laminate 1 and/or the panel member 16, the elastically stretchable member 17 generally has a stretch stress of 50~1500 g, preferably 100~1000 g and more preferably 150~800 g as measured with the elastically member 17 being stretched from its initial length of 100 mm by the same length.

FIG. 4 illustrates a second embodiment of the invention. Referring to FIG. 4, the panel member 16 has its transversely opposite side edges lying short of the transversely opposite side edges of the deformation assisting means 13 and secured to the backsheet 7 by means of hot melt adhesive means 19a. The elastically stretchable member 17 also is secured to the panel member 16 by means of hot melt adhesive means 19b in the proximity of the transversely opposite side edges of the panel member 16. Obviously, such securing may be achieved by heat-sealing instead of using the hot melt adhesive means 19a, 19b.

FIG. 5 illustrates a third embodiment of the invention. Referring to FIG. 5, the deformation inducing means 15 is secured to the outer surface of the backsheet 7 utilizing a series of compressed dots (i.e., heat-sealed dots formed by embossing) 13a serving as the deformation assisting means 13. Such securing may be achieved by means of hot melt adhesive means instead of the heat-sealing. The deformation inducing means 15 may have its transversely opposite ends lying short of the transversely opposite side edges of the deformation assisting means 13. As will be readily understood, the embodiment illustrated by FIG. 5 is characterized in that, in a region of the absorbent laminate 1 defining the convexly deformable zone 12, the topsheet 6, the core 8 and the backsheet 7 are convexly deformed together under the effect of the deformation inducing means 15.

Figure 6:
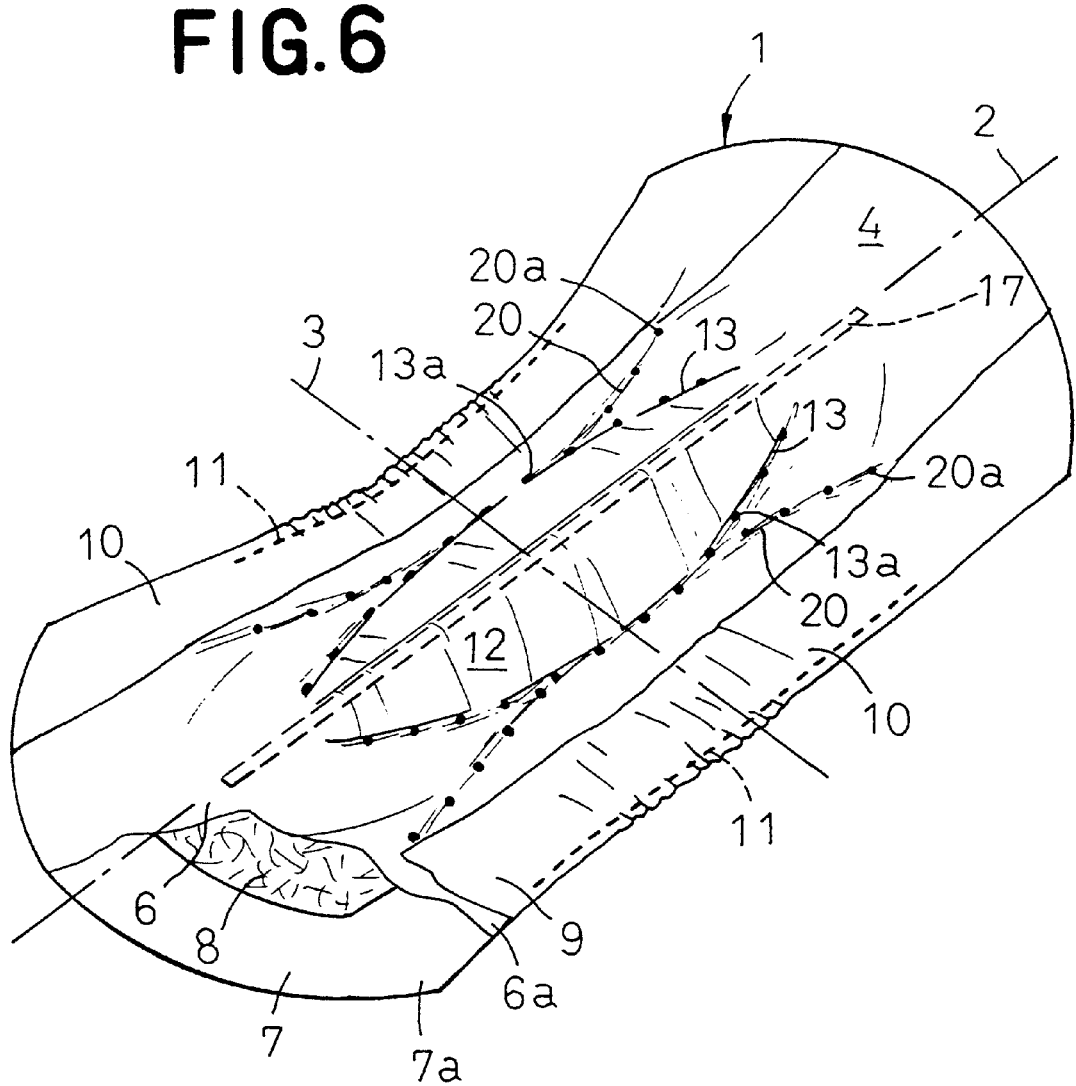
FIG. 6 is a perspective view of a sanitary napkin according to a fourth embodiment of the invention.
Figure 7:
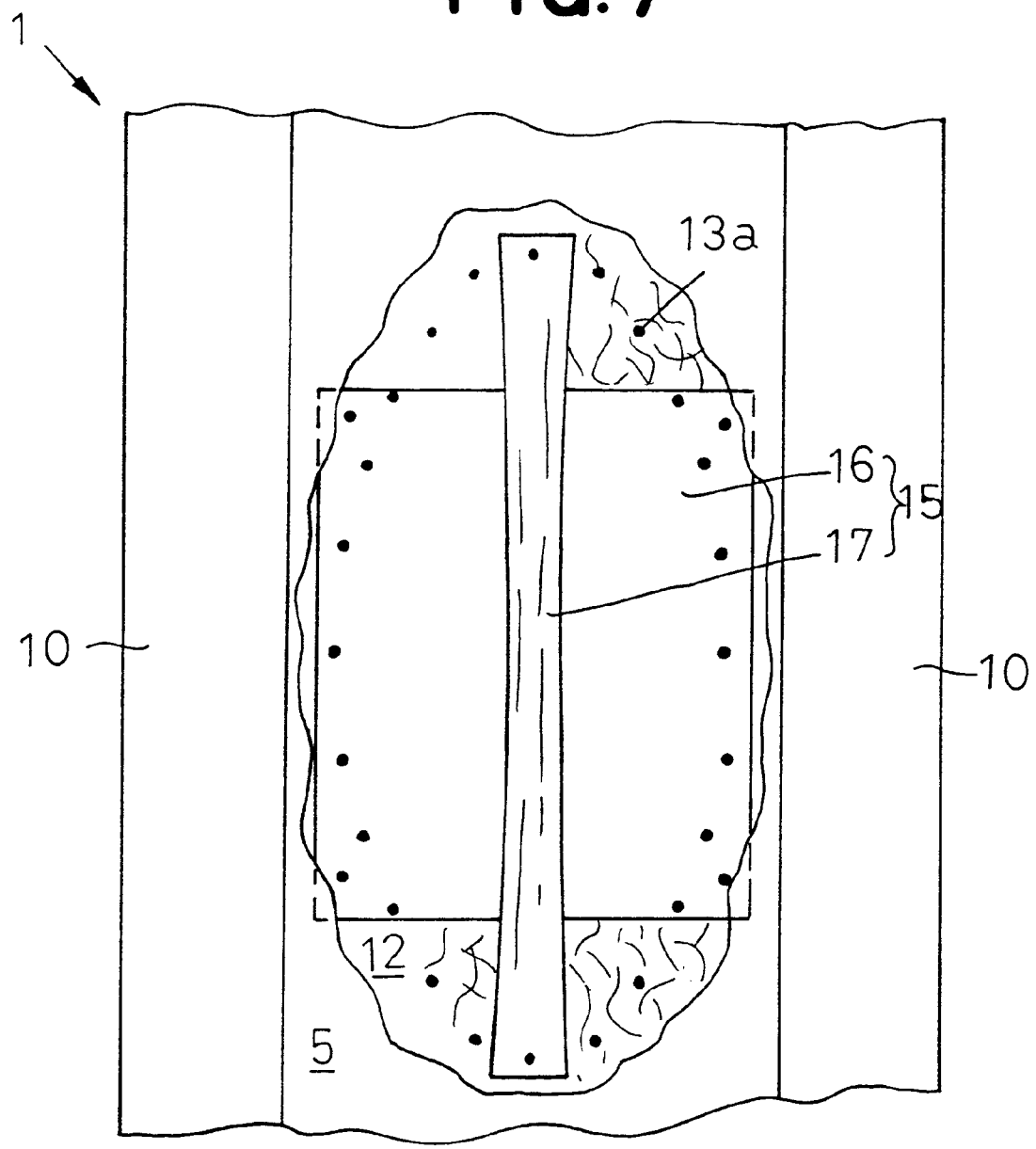
FIG. 7 is a plan view showing a bottom side of the napkin partly cutaway, shown in FIG. 6.
Figure 8:
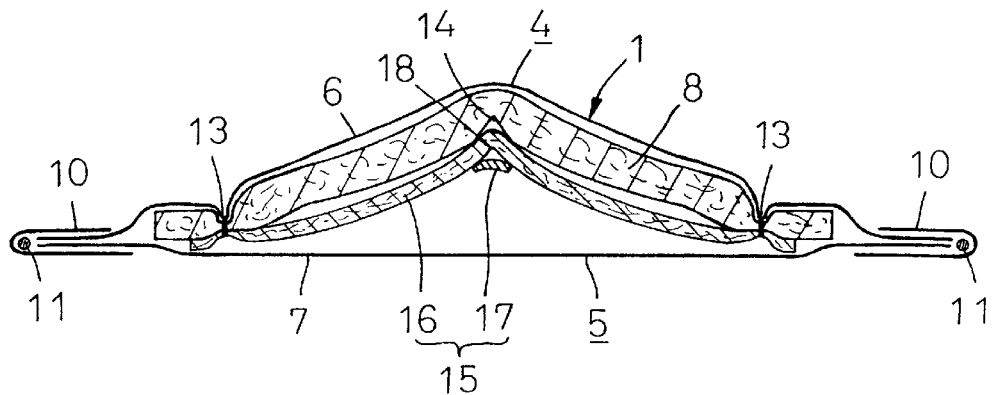
FIG. 8 is a schematic sectional view of the napkin, shown in FIG. 6, taken along a line diving the napkin in front and rear halves.

FIGS. 6–8 illustrates a fourth embodiment of the invention. The elastically stretchable member 17 extends outward beyond longitudinally opposite ends of the panel member 16 and is secured to the core 8 in the proximity of longitudinally opposite ends of the core 8 with a longitudinal tension. It is also possible to secure the elastically stretchable member 17 to the panel member 16 in the proximity of the longitudinally opposite ends of said panel member 16. Consequently, the panel member 16 is convexly deformed toward the skin-contactable side 4 along the potential fold of the middle portion 18 as the elastically stretchable member 17 contracts.

Figure 9:
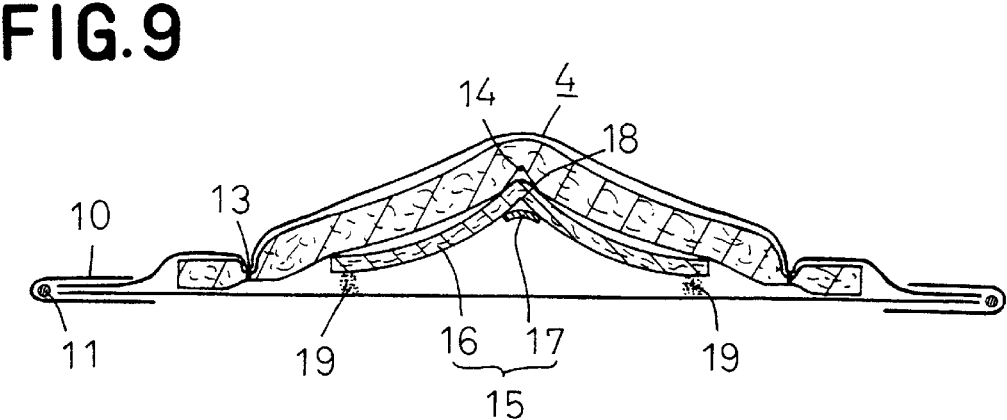
FIG. 9 is a view similar to FIG. 8 but showing a sanitary napkin according to a fifth embodiment of the invention.

FIG. 9 illustrates a fifth embodiment of the invention. Referring to FIG. 9, the panel member 16 has its transversely opposite side edges lying short of the transversely opposite side edges of the deformation assisting means 13 and secured to the backsheet 7 by means of hot melt adhesive means 19. Obviously, such securing may be achieved also by heat-sealing.

Figure 10:
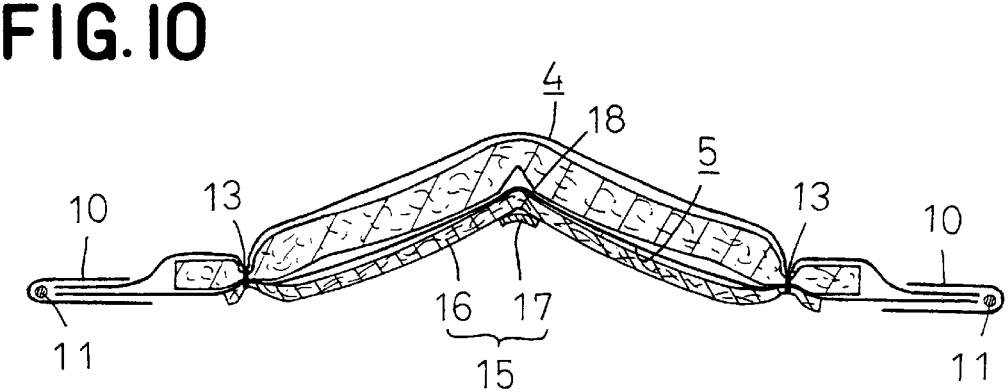
FIG. 10 is a view similar to FIG. 8 but showing a sanitary napkin according to a six embodiment of the invention.

FIG. 10 illustrates a sixth embodiment of the inventions. Referring to FIG. 10, the deformation inducing means 15 is secured to the outer surface of the backsheet 7 utilizing a series of compressed dots (i.e., heat-sealed dots formed by embossing) 13a serving as the deformation assisting means 13. Such securing may be achieved by mean of hot melt adhesive means instead of the heat-sealing. The deformation inducing means 15 may have its transversely opposite ends lying short of the transversely opposite side edges of the deformation assisting means 13. As will be readily understood, the embodiment illustrated by FIG. 10 is characterized in that, in a region of the absorbent laminate 1 defining the convexly deformable zone 12, the topsheet 6, the core 8 and the backsheet 7 are convexly deformed together under the effect of the deformation inducing means 15.

The absorbent article according to the invention includes the deformation inducing means formed separately of the absorbent laminate itself and provided on the skin-noncontactable side of the laminate. The deformation inducing means have hydrophobicity as well as rigidity required for its desired function. The function of the deformation inducing means ensures the region of the laminate defining the convexly deformable zone to be convexly deformed toward the wearer's skin even when the laminate is wetted with body fluids such as menstrual discharge. In consequence, a fitness of the article to the wearer's external genital organs is improved and thereby a leakage of menstrual discharge is effectively avoided.

The deformation inducing means comprise the hydrophobic panel member which is deformable to its substantially flat state and the elastically stretchable member. Cooperation of these two members causes the region of the absorbent laminate defining the convexly deformable zone to be convexly deformed. Such a unique arrangement can offer various advantages. For example, the absorbent laminate and the deformation inducing means can be packaged together in the form of a substantially flat article. Even after the article has been packaged in the flat state, said convexly deformed state can be restored as the elastically stretchable member contracts again as soon as the package is opened.

What is claimed is:

1. An absorbent article having a longitudinal axis, a skin-contactable side and a skin-noncontactable side, said absorbent article comprises:

an absorbent laminate and deformation inducing means provided adjacent said skin-noncontactable side so as to convexly deform said absorbent laminate toward said skin-contactable side;

said absorbent laminate including a convexly deformable zone which lies on both sides of said longitudinal axis so as to be contoured symmetrically with respect to said longitudinal axis, and deformation assisting means formed on both sides of said convexly deformable zone;

said deformation inducing means including a panel member and an elastically stretchable member which has transverse ends thereof secured in a vicinity of said deformation assisting means to said panel member so as to convexly deform said panel member about said longitudinal axis toward said skin-contactable side as said elastically stretchable member elastically contracts, respective regions of said absorbent laminate and said deformation inducing means which have been convexly deformed are deformable to substantially flat states against a contractile force of said elastically stretchable member when a contacting pressure directed from said skin-contactable side toward said skin-noncontactable side is exerted on said article.

2. The article according to claim 1, wherein a convexly deformable zone defined in said absorbent laminate lies on both sides of said longitudinal center line so as to be contoured symmetrically with respect to said longitudinal center line and includes first deformation assisting means extending on said skin-noncontactable side along a section of said longitudinal center line.

3. The article according to claim 2, wherein said first deformation assisting means comprise compressed grooves, slits or series of compressed dots.

4. The article according to claim 2, wherein said convexly deformable zone in said absorbent laminate further includes second deformation assisting means which divert at opposite ends outwardly from said first deformation assisting means.

5. The article according to claim 4, wherein said second deformation assisting means comprise a series of compressed dots or compressed grooves.

6. The article according to claim 1, wherein said panel member has a cantilever-measured value of 40~100 mm as measured according to JIS.

7. The article according to claim 1, wherein said panel member is selected from the group consisting of paper sheets, fibrous sheets, foamed plastic sheets, non-foamed plastic sheets, and laminates consisting of mixtures thereof.

8. The article according to claim 1, wherein said panel member has a width narrower than a width of said absorbent laminate both measured along said transverse center line and lies short inwardly of transversely opposite side edges of said absorbent laminate.

9. The article according to claim 1, wherein said elastically stretchable member is secured to said panel member at two or more portions thereof in the vicinity of its transversely opposite side edges.

10. The article according to claim 1, wherein said elastically stretchable member has a stretch stress of 50~1500 g.

11. The article according to claim 1, wherein said absorbent laminate comprises a liquid-permeable topsheet, a liquid-impermeable backsheet and a liquid-absorbent core disposed between said topsheet and said backsheet.

12. The article according to claim 11, wherein surfaces of said liquid-absorbent core and said backsheet opposed to each other at least in said convexly deformed portion of the absorbent laminate are.

13. The article according to claim 11, wherein said deformation inducing means are disposed between said liquid-absorbent core and said backsheet and secured to said liquid-absorbent core at two or more portions thereof in the proximity of its transversely opposite side edges.

14. The article according to claim 4, wherein said absorbent laminate and said deformation inducing means are secured together by means of said second deformation assisting means.

* * * * *

UNITED STATES PATENT AND TRADEMARK OFFICE
CERTIFICATE OF CORRECTION

PATENT NO.     : 6,394,989 B2
DATED          : May 28, 2002
INVENTOR(S)    : Satoshi Mizutani It is certified that error appears in the above-identified patent and that said Letters Patent is hereby corrected as shown below:

<u>Column 8,</u>
Line 20, after the word "are" please insert -- separable from each other --

Signed and Sealed this

Eighth Day of October, 2002

*Attest:*

*Attesting Officer*

JAMES E. ROGAN
*Director of the United States Patent and Trademark Office*